(12) United States Patent
Forshee et al.

(10) Patent No.: US 8,129,190 B2
(45) Date of Patent: Mar. 6, 2012

(54) TAGGED PETROLEUM PRODUCTS AND METHODS OF DETECTING SAME

(75) Inventors: Philip Forshee, Dallas, TX (US); Peter Kottenstette, Plano, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 1020 days.

(21) Appl. No.: 11/561,119

(22) Filed: Nov. 17, 2006

(65) Prior Publication Data

US 2008/0118982 A1    May 22, 2008

(51) Int. Cl.
*G01N 33/00* (2006.01)
*C01L 1/04* (2006.01)

(52) U.S. Cl. ............................ 436/56; 436/139; 208/15

(58) Field of Classification Search .................. 436/56, 436/139; 208/15; 552/276, 277, 279, 280, 552/281
See application file for complete search history.

(56) References Cited

U.S. PATENT DOCUMENTS 2,051,121 A    8/1936   John
(Continued)

FOREIGN PATENT DOCUMENTS

DE    38 35 489 A1    4/1990
(Continued)

OTHER PUBLICATIONS

Letter from Foreign Associate enclosing patent certificate, mailed Dec. 2, 2009, 1 page.
(Continued)

*Primary Examiner* — Robert J Hill, Jr.
*Assistant Examiner* — Dwan A Gerido
(74) *Attorney, Agent, or Firm* — Kelly Kordzik; Matheson Keys Garsson & Kordzik PLLC

(57) ABSTRACT

Tagged products (including tagged petroleum products) and methods of detecting the same are disclosed. The tagged petroleum products are tagged with a violanthrone, e.g., a substituted violanthrone and/or an isoviolanthrone, e.g., a substituted isoviolanthrone.

10 Claims, 17 Drawing Sheets violanthrone (1)

isoviolanthrone (1')

U.S. PATENT DOCUMENTS

| | | | |
|---|---|---|---|
| 2,135,259 A * | 11/1938 | Neresheimer et al. | 552/279 |
| 3,630,941 A | 12/1971 | Bergmark | |
| 4,076,645 A | 2/1978 | Vega | |
| 4,198,529 A | 4/1980 | Grelat et al. | |
| 4,313,843 A | 2/1982 | Bollyky et al. | |
| 4,486,587 A * | 12/1984 | Seybold | 544/99 |
| 4,678,608 A | 7/1987 | Dugliss | |
| 5,525,516 A | 6/1996 | Krutak | |
| 5,554,774 A | 9/1996 | Bergmann et al. | |
| 5,710,046 A * | 1/1998 | Rutledge et al. | 436/56 |
| 5,723,338 A | 3/1998 | Rutledge | |
| 5,804,447 A | 9/1998 | Albert | |
| 5,831,593 A | 11/1998 | Rutledge | |
| 5,879,946 A | 3/1999 | Weeks | |
| 5,928,954 A | 7/1999 | Rutledge | |
| 5,998,211 A | 12/1999 | Albert | |
| 6,002,056 A | 12/1999 | Smith et al. | |
| 6,215,008 B1 * | 4/2001 | Heffron | 552/276 |
| 6,274,381 B1 | 8/2001 | Pauls et al. | |
| 6,312,958 B1 | 11/2001 | Meyer | |
| 6,340,745 B1 | 1/2002 | Meyer | |
| 6,811,575 B2 | 11/2004 | Ho | |
| 2004/0106526 A1 | 6/2004 | Ho | |
| 2004/0110997 A1 | 6/2004 | Ho | |
| 2004/0250469 A1 | 12/2004 | Baxter | |

FOREIGN PATENT DOCUMENTS

| | | |
|---|---|---|
| ZA | 2007/07354 | 4/2009 |

OTHER PUBLICATIONS

Hihara, et al; "Photo-oxidation and -reduction of vat dyes on water-swollen cellulose and their lightfastness on dry cellulose"; Dyes and Pigments 53; no month, 2002; pp. 153-177; Elsevier Science Ltd.; New York, US.

European Patent Office; European Extended Search Report; Dec. 2, 2010; European Patent Office, Munich, Germany.

* cited by examiner

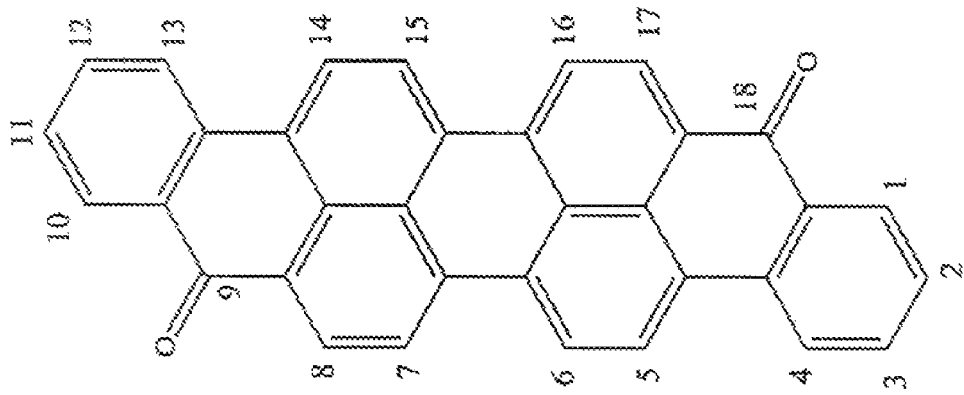
FIG. 1B isoviolanthrone (1')
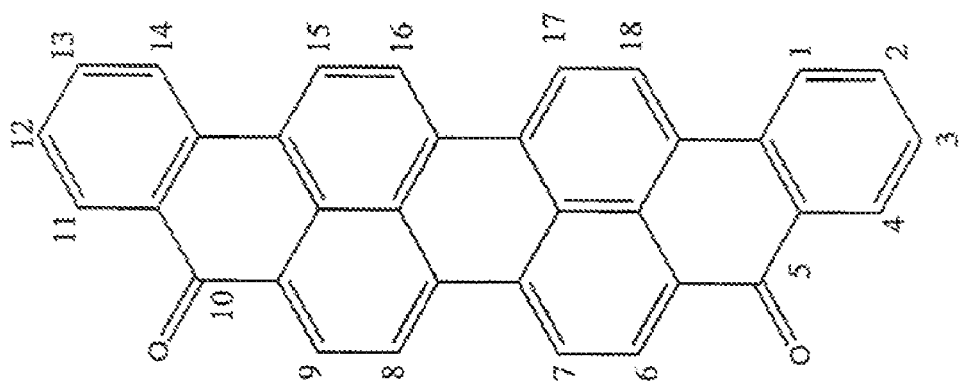
FIG. 1A violanthrone (1)

n = 0 – 8, inclusive

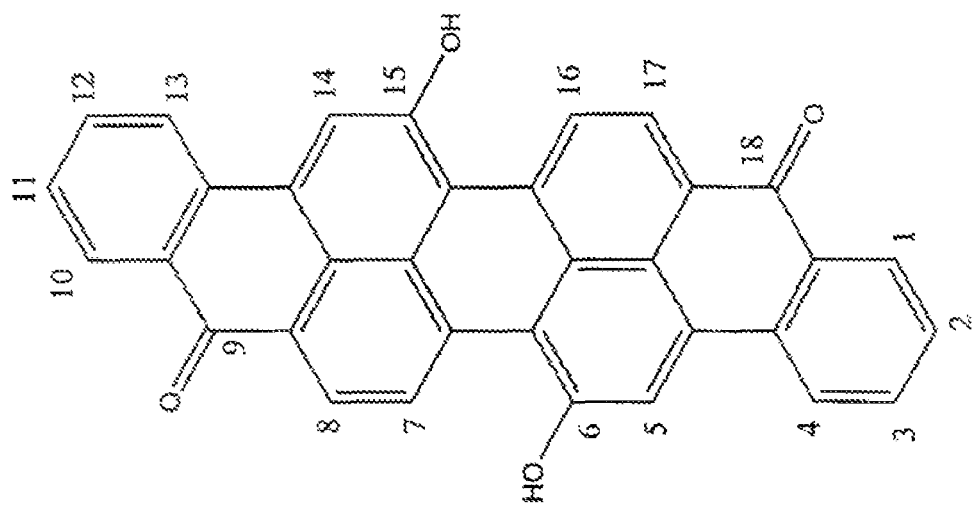
FIG. 5B 6,15-dihydroxyisoviolanthrone (2')
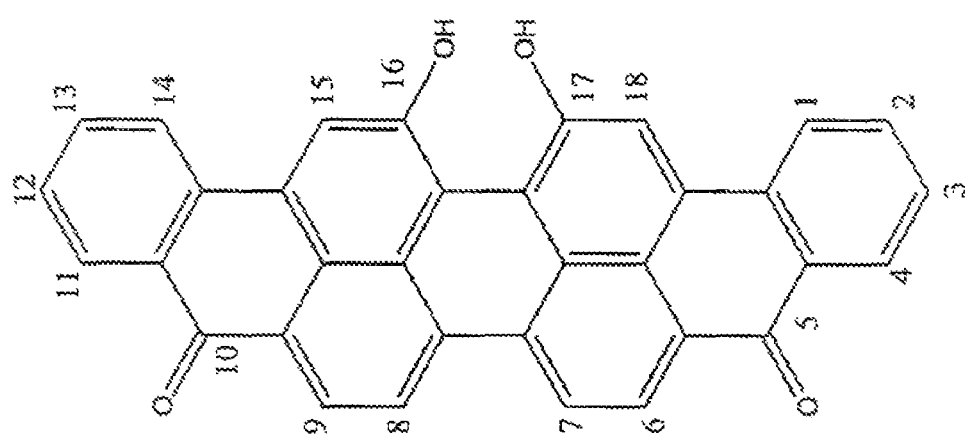
FIG. 5A 16,17-dihydroxyviolanthrone (2)

1,14,16,17-tetrahydroxyviolanthrone (3)

TAGGED PETROLEUM PRODUCTS AND METHODS OF DETECTING SAME

TECHNICAL FIELD

This invention relates to tagged petroleum products, and also to methods of detecting the same.

BACKGROUND

For a myriad of reasons, attempts are often made to copy or imitate products for commercial gain. While counterfeit products will often appear visually identical to the original products, the counterfeit products often will not authentically posses the properties that impart the favorable attributes of the original. Such deception can cause harm, sometimes irreparable harm, such as to the brand name or brand image of the producer of the original product. Significant commercial gain can also be obtained by counterfeiters through the dilution of the original products with a readily available, less expensive material.

For instance, petroleum products can be tagged for identification purposes with coloring agents to provide a distinct color visually perceptible to the naked eye. Such tagging allows these tagged petroleum products to be distinguished from other petroleum products for a number of reasons, including to distinguish the manufacturer, to differentiate similar fuels taxed at different rates, to identify various grades of the fuels, to render untraceable the adulteration, counterfeiting, and/or misuse of the petroleum product, and to make it hard to detect other unlawful practices (such as tax evasion and theft).

For lower taxed petroleum products, governments have commonly required these to be colored so that they may be distinguished from similar fuels subject to higher tax rates and to assist in the detection of tax evasion. Petroleum products are also colored by oil companies that market brand name products (such as gasoline) to prevent misuse by their dealers. Such oil companies must insure that their branded products meet specifications regarding volatility and octane specifications, and they also provide their products with effective packages containing detergents and other additives. To do so, there is a price the oil companies must pay. In turn, consumers recognize the value of these name brand products and are willing to purchase the petroleum products at a higher price due to the increase quality. By imitating or diluting the branded product, a dealer can take advantage of consumers and reap increase profits while selling an inferior product.

It is also known that coloring agents are not always reliable. The coloring agent may be removed by relatively simple methods such as acid/base reactions. Or natural substances or the additives may obscure the coloring agents and make them difficult to detect. Another problem a high dosage level of the coloring agent is need for detection, which can create increased costs and other problems.

What is needed is a tagging compound that can be added to an original product to provide for a more secure technique for the field determination of authenticity of the product. The tagging compound should not be easily removable. Also, it would be beneficial if little training of the monitoring personnel is required and the tagging compound used for marking or tagging the original product was relatively inexpensive.

SUMMARY

This invention relates to tagged petroleum products, and also to methods of detecting the same. For example, the tagged petroleum product can be tagged with a violanthrone (e.g., a substituted violanthrone) or an isoviolanthrone (e.g., a substituted isoviolanthrone). FIGS. 1A and 1B show structures for violanthrone (1) and isoviolanthrone (1'), respectively.

In one aspect, the invention features tagged products that include a petroleum product and a tagging compound of Structure I and/or Structure II, as shown in FIGS. 2A and 2B, respectively. In Structure I and Structure II, each R of $R_n$ is independently OH, SH, $NH_2$, $NO_2$, F, Cl, Br, I or moiety that includes between 1 to 36 carbon atoms, inclusive. Each n is an integer between 0 and 8, inclusive.

In some embodiments of the invention, to enable their detection, a concentration of at least about 1 ppb by weight of the tagging compound is dissolved in the petroleum product.

In some embodiments, at least one R ($R_z$) is a moiety that includes between 1 and 36 carbon atoms, inclusive. In such embodiments, $R_z$ can further include at least one N, O, S, F, Cl, Br, or I atom.

In some embodiments at least one R ($R_z$) is a moiety that includes between 1 and 36 carbon atoms, inclusive. In some particular embodiments, $R_z$ includes only carbon and hydrogen atoms. For example, $R_z$ can be C1-C21 alkyl, C1-C8 cylcoaklyl, C1-C21 alkenyl, C1-C10 aryl or C1-C21 alkylaryl.

In some other embodiments, at least one R ($R_z$) is a moiety that includes between 1 and 36 carbon atoms, inclusive. In some particular embodiments, the moiety only includes carbon, hydrogen and oxygen. For example, the moiety that includes only carbon hydrogen and oxygen can include an ether or an ester group, e.g., one that is attached directly to the core structure.

In some instances, the tagging compound is of Structure III, as shown in FIG. 3A. In such instances, $R_1$ and $R_2$ can be, e.g., each independently a moiety that includes between 1 and 36 carbon atoms, inclusive.

In some implementations, the tagging compound is of Structure IV, as shown in FIG. 3B. In such implementations, $R_3$ and $R_4$ can be, e.g., each independently a moiety that includes between 1 and 36 carbon atoms, inclusive.

In some other implementations, the tagging compound is of Structure V, as shown in FIG. 4. In such implementations, $R_5$, $R_6$, $R_7$ and $R_8$ can be, e.g., each independently a moiety that includes between 1 and 36 carbon atoms, inclusive.

In some embodiments, at least one R ($R_2$) is a moiety that includes between 1 and 36 carbon atoms, inclusive. In such embodiments, the moiety can define a ring, e.g., one, two, three or four rings. For example, the rings can be 5-6, or 7-membered rings. For example, the ring can be carbocyclic or heterocyclic.

Examples of petroleum products include gasoline, kerosene, diesel, naphtha, lubricant oil, furnace oil, or mixtures of any of these, e.g., mixtures of gasoline and kerosene, which is more commonly known as military jet fuel or JP4.

In some embodiments, the concentration of the tagging compound in the tagged product is between about 0.001 ppm and about 1000 ppm on a weight basis. Low concentrations are desirable for cost and product integrity and/or performance reasons.

In other embodiments, the tagging compound responds to near infrared light. For example, the tagging compound can absorb and/or emit near infrared light.

In another aspect, the invention features methods that include selecting a sample of a tagged product in which the tagged product includes a petroleum product and a tagging compound of Structure I and/or Structure II; and detecting the tagging compound in the tagged product.

In some embodiments, the tagging compound is dissolved in the product at a concentration of at least about 1 ppb by weight. This can allow for the tagging compound to be easily detected.

For example, the detecting step can include detecting a response of the tagging compound. For instance, the response can be (i) emissions from the tagging compound, (ii) absorbances by the tagging compound or (iii) emissions from a reaction product formed by reacting the tagging compound with another compound.

In some embodiments, the response includes an emission from and/or an absorbance by the tagging compound. For example, emission and/or absorbance can occur at a wavelength between about 500 nm and about 900 nm.

Although sometimes just detecting the presence of the tagging compound is desired, in other embodiments, it is advantageous to quantitate the response.

In another aspect, the invention features a tagged product that includes a petroleum product and a first tagging compound dissolved in the petroleum product. The first tagging compound can be a non-substituted violanthrone, a substituted violanthrone, a non-substituted isoviolanthrone, a substituted isoviolanthrone or combinations thereof.

In some embodiments, the first tagging compound has a solubility of greater than about 0.5 percent by weight in toluene, e.g., greater that 1 percent by weight in toluene. High solubility can be desirable because concentrates of the violanthrone or isoviolanthrone can be produced. Concentrates make it easy to add a small amount of the tagging compound to a larger volume of a petroleum product, e.g., during online blending of gasoline or jet fuel.

In some embodiments, the first tagging compound is substituted with at least one moiety that comprises between 1 and 36 carbon atoms, inclusive.

In some implementations, the tagged product further includes a second tagging compound dissolved in the petroleum product along with the first tagging compound. In such implementations, the second tagging compound, which is different from the first tagging compound, is a non-substituted violanthrone, a substituted violanthrone, a non-substituted isoviolanthrone, a substituted isoviolanthrone or combinations thereof.

In some embodiments, the second tagging compound has a solubility of greater than about 0.5 percent by weight in toluene, e.g., greater than 1 percent by weight in toluene.

For detection, it is desirable that the first tagging compound be dissolved in the petroleum product at a concentration of at least about 1 ppb by weight, and that the second tagging compound also be dissolved in the petroleum product at a concentration of at least about 1 ppb by weight.

In another aspect, the invention features methods that include selecting a sample of a tagged product that includes a petroleum product; collecting absorbance and/or emission data on the tagged product; and comparing the collected data to data for tagging compounds to identify a source of the tagged product. The data for tagging compounds is data for compounds of Structure I and/or Structure II. For example, the data collected on the sample can be compared to a library having wavelength data and concentration versus absorbance data for compounds of Structure I and/or Structure II.

Embodiments and/or aspects can have any one of, or combinations of, the following advantages. The tagging compounds are combustible. The tagging compounds do not significantly reduce the performance of the petroleum products to which they are added to, nor do they appreciably change the physical and/or chemical properties of the petroleum products with which they are added to. The tagging compounds are detectible in the tagged petroleum product at a low concentration, e.g., above 1 ppb by weight, e.g., from about 0.001 ppm by weight to about 1000 ppm by weight. The compounds are readily soluble in petroleum products, e.g., aromatic petroleum products, such as benzene, toluene, a xylene, a mesitylene, Aromatic 100 (C9-C10 aromatic mixture). Aromatic 150 (C10-C11 aromatic mixture) or Aromatic 200 (C10-C14 aromatic mixture). High solubility can allow for the preparation of concentrates, which are a convenient form to add to a petroleum product. For example, the tagging compounds can have a solubility greater than 0.25 weight percent in the petroleum product, e.g., greater than 0.5 percent, greater that 1 percent, 1.5 percent, 2.0 percent, or even greater than 5 percent by weight in the petroleum product.

Furthermore, the tagging compounds are chemically stable, e.g., not prone to oxidation, degradation and/or thermal rearrangements. The tagging compounds do not tend to crystallize and/or agglomerate in a petroleum product. The tagging compounds can be detected and their concentration quantitated using commercially available fluorometers or infrared spectrometers, e.g., near infrared spectrometers. Mixtures of the tagging compounds can be used to make counterfeiting even more difficult because the ratios of the compounds can be predetermined, resulting in a unique "spectral fingerprint." The tagging compounds are relatively inexpensive to prepare.

Optionally, the tagging compounds can be detected by measuring chemiluminescence generated from a reaction product of the tagging compound and a reactant, such as a strong oxidizing agent, e.g., an organic peroxyoxalates, optionally in combination with a peroxide. Many of the tagging compounds absorb and/or emit in the near infrared region of the spectrum, e.g., between about 650 nm and about 900 nm, but have little or no absorbance in the visible region of the spectrum, e.g., from about 400 nm to about 650 nm, making the tagging compounds "invisible" to the naked eye. As a result, the tagging compounds do not appreciably change the color of petroleum product to which they are added.

As used herein, "petroleum products" are hydrocarbon compounds or mixtures derived from processing natural gas or petroleum. This processing typically occurs at oil refineries, gas processing plants, and gasoline plants. Petroleum products include, e.g., butane, propane, benzene, toluene, gasoline, heating oil, aviation fuel, kerosine and diesel fuel. Also included are hydrocarbon feedstocks, such as ethylene and propylene. Intermediate and finished products manufactured at petrochemical plants by further processing hydrocarbon feedstocks, e.g., by the addition of chlorine, nitrogen, or oxygen to the hydrocarbon feedstocks are not considered to be petroleum products. For example, ethylene glycol, which is used in car antifreeze is not considered a petroleum product.

All publications, patent applications, patents, and other references mentioned herein are incorporated by reference in their entirety for all that they contain.

Other features and advantages of the invention will be apparent from the following detailed description, and from the claims.

DESCRIPTION OF DRAWINGS

FIGS. 1A and 1B show structures for violanthrone (1) and isoviolanthrone (1'), respectively.

FIGS. 5A and 5B show structures for 16,17-dihydroxysubstituted violanthrone (2) and 6,15-dihydroxysubstuted isoviolanthrone (2'), respectively.

DETAILED DESCRIPTION

Violanthrones (e.g., substituted violanthrones), isoviolanthrones (e.g., substituted isoviolanthrones) or combinations thereof are typically near infrared fluorophores that are highly effective tagging compounds for the identification of petroleum products. Generally, the violanthrone and isoviolanthrone tagging compounds have adequate thermal stability, and little light absorption in the visible region of the spectrum. As such, the tagging compounds impart little or no color to the petroleum product to which they mixed. Advantageously, the tagging compounds also have a strong absorption and/or emission in the near infrared region of the spectrum (e.g., wavelengths of about 670 nm-2500 nm), allowing for their easy detection.

Referring now to FIG. 1A, the simplest of the violanthrone family is violanthrone (1) itself, which has nine fused six-membered rings and carbonyl groups that occupy positions 5 and 10. The violanthrone (1) molecule has a highly delocalized $\pi$-electron system, which forces the molecure to a planar configuration. Similarly, the simplest of the isoviolanthrone family is isoviolanthrone (1') itselt, which also has nine fused six-membered rings (shown in FIG. 1B). In the case of isoviolanthrone (1'), the carbonyl groups occupy positions 9 and 18, on opposite sides of the planar structure.

Figure 2A:
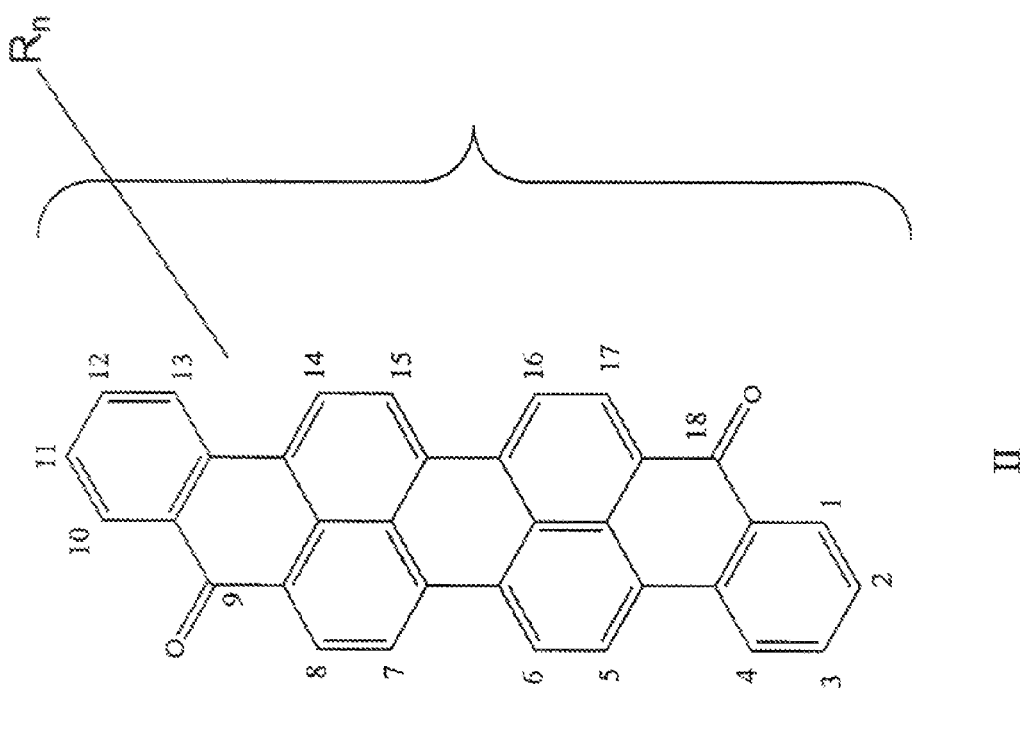
FIGS. 2A and 2B show structures for substituted violanthrones (I) and substituted isoviolanthrones (II), respectively.
Figure 2B:
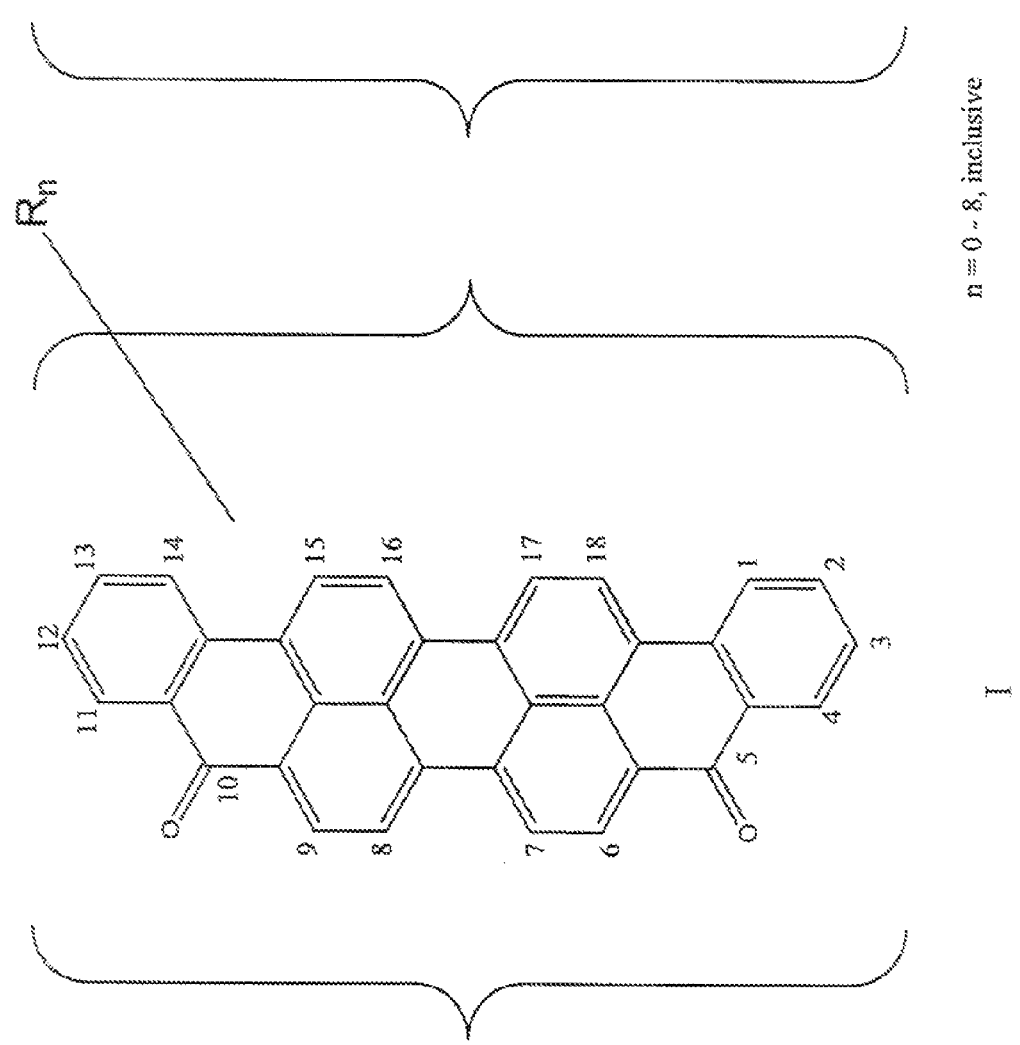

Generally, a tagged product includes a petroleum product, and one or more violanthrone and/or isoviolanthrone tagging compounds. Referring now to FIGS. 2A and 2B, in some embodiments, the tagging compounds are represented by Structure I and Structure II, respectively. In such compounds, each R and $R_n$ is independently OH, SH, $NH_2$, $NO_2$, F, Cl, Br, I or a moiety that includes between 1 and 36 carbon atoms, inclusive. In the representations shown, n is an integer between 0 and 8, inclusive.

In some embodiments, the tagged product has a concentration of at least about 1 ppb by weight of the tagging compound dissolved in the petroleum product. For example, the concentration can be greater than about 2, 3, 10, 25, 50, 75, 100, or greater than about 250 ppb by weight. For example, for cost reasons and for reducing the likelihood that the tagging compound will reduce the performance of the petroleum product, the concentration of the tagging compound in a finished petroleum product is advantageously less than about 2500 ppb by weight, e.g., less than 2000 ppb, 1500 ppb, or less than 1000 ppb by weight.

In some embodiments, n is between 1 and 6, e.g., between 2 and 5.

In some instances, at least one R ($R_z$) is a moiety that includes between 1 and 36 carbon atoms, inclusive. In such instances, the one or more moieties that include between 1 and 36 carbon atoms can further include one or more N, O, S, F, Cl, Br, or I atoms. For example, each R can be moiety that includes between 1 and 36 carbon atoms and includes only carbon, hydrogen and oxygen atoms. For example, each R can include one or more ester or ether groups. For example, the ester or ether group can be bonded directly to the violanthrone or isoviolanthrone core or it can be along R.

In some embodiments, at least one R ($R_z$) is a moiety that comprises between 1 and 36 carbon atoms, inclusive, and includes only carbon and hydrogen atoms (i.e. is a hydrocarbon fragment). For example, the hydrocarbon fragment can be a C1-C21 alkyl, a C1-C8 cylcoalkyl, a C1-C21 alkenyl, a C1-C10 aryl, or a C1-C21 alkylaryl.

In some embodiments, at least one R ($R_z$) is a moiety that includes between 1 and 36 carbon atoms, and at least some of the carbon atoms define one or more ring systems. For example, the defined rings can be, e.g., 3-, 4-, 5-, 6-, 7-, 8-, or 9-membered rings. For example, the defined rings can be carbocylic or hetrocyclic.

Figure 3B:
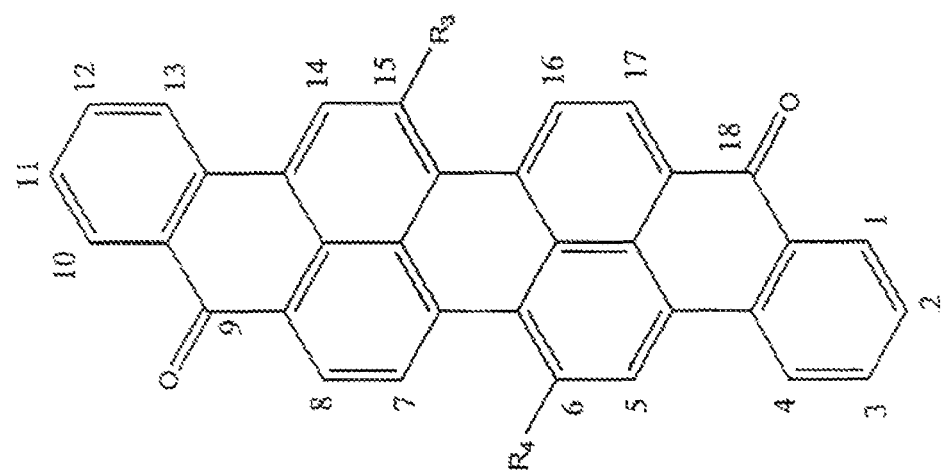
FIGS. 3A and 3B show structures for 16,17-disubstituted violanthrones (III) and 6,15-disubstuted isoviolanthrones, respectively.
Figure 3A:
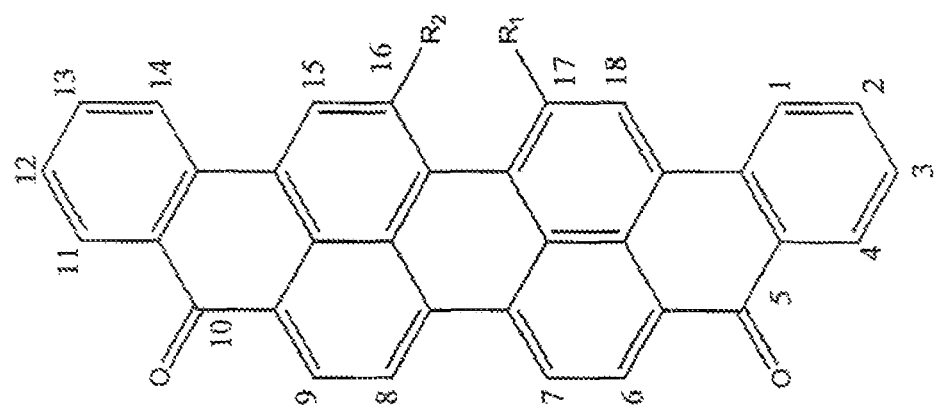

Referring now to FIG. 3A, in some embodiments, the tagging compound is a 16,17-disubstituted violanthrone represented by Structure III. In such instances, $R_1$ and $R_2$ can, e.g., each be independently a moiety that includes between 1 and 36 carbon atoms, inclusive. For example, each can independently represent an ester, an ether or a hydrocarbon fragment, or can include an ester group, an ether group or a hydrocarbon fragment. In some embodiments, the tagging compound is a 6,15-disubstituted isoviolanthrone represented by Structure IV (FIG. 3B). In such instances, $R_3$ and $R_4$ can each, e.g., be independently a moiety that includes between 1 and 36 carbon atoms, inclusive. For example, each can independently represent an ester, an ether or a hydrocarbon fragment, or can include an ester group, an ether group or a hydrocarbon fragment.

Figure 4:
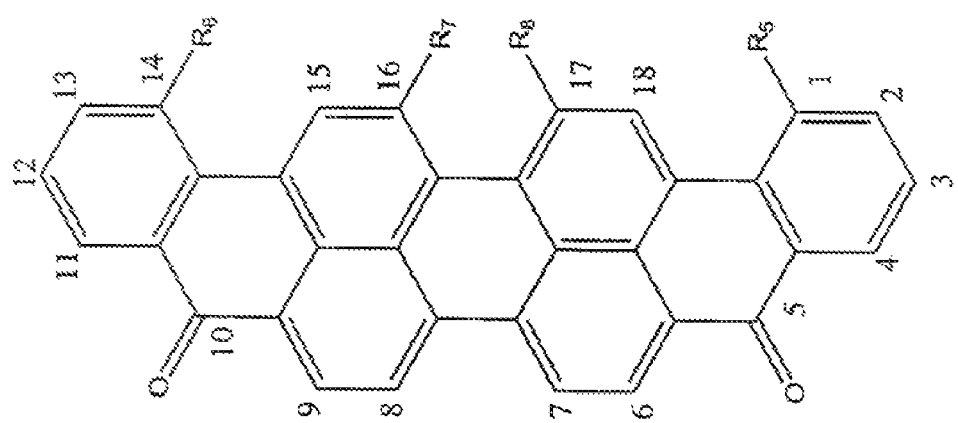
FIG. 4 shows the structure for 1,14,16,17-tetrasubstituted violanthrones (V).

Referring now to FIG. 4, in some embodiments, the tagging compound is a 1,14,16,17-tetrasubtituted violanthrone, represented by Structure V. In such instances, $R_5$, $R_6$, $R_7$ and $R_8$ can, e.g., each be independently a moiety that includes between 1 and 36 carbon atoms, inclusive. For example, each can independently represent an ester, an ether or a hydrocarbon fragment, or can include an ester group, an ether group or a hydrocarbon fragment.

Examples of petroleum products to which the tagging compounds can be added include gasoline, kerosene, diesel, naphtha, lubricant oil, benzene concentrate, butadiene monomer, isooctane, furnace oil, propylene monomer, liquefied petroleum gas, petroleum waxes and mineral oil.

Figure 6:
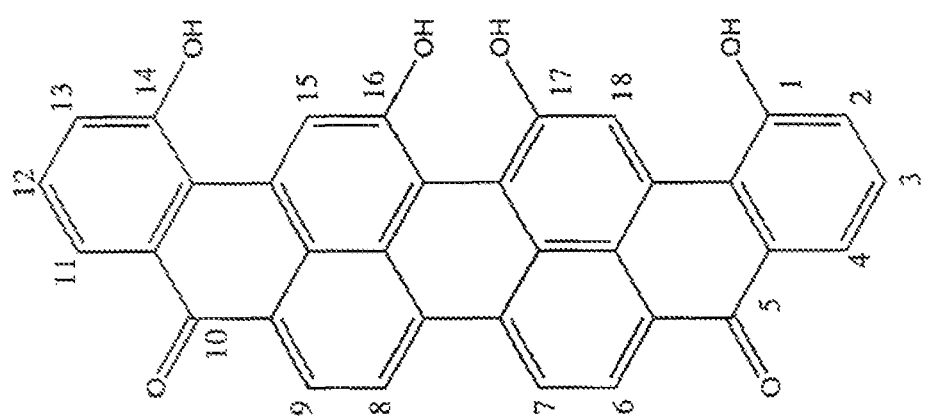
FIG. 6 shows the structure for 1,14,16,17-tetrahydroxysubstituted violanthrone (3).

Referring now to FIGS. 5A, 5B and 6, in specific embodiments, the violanthrone or isoviolanthrone is 16,17-dihydroxyviolanthrone (2), 6,15-dihydroxyisoviolanthrone (2') or 1,14,16,17-tetrahydroxyviolanthrone (3). Compounds (2), (2') and (3) are convenient starting materials for various substituted violanthrones or isoviolanthrones. Compound (2), for example, is commercially available from the Pfaltz and Bauer Chemical Company.

Figure 7:
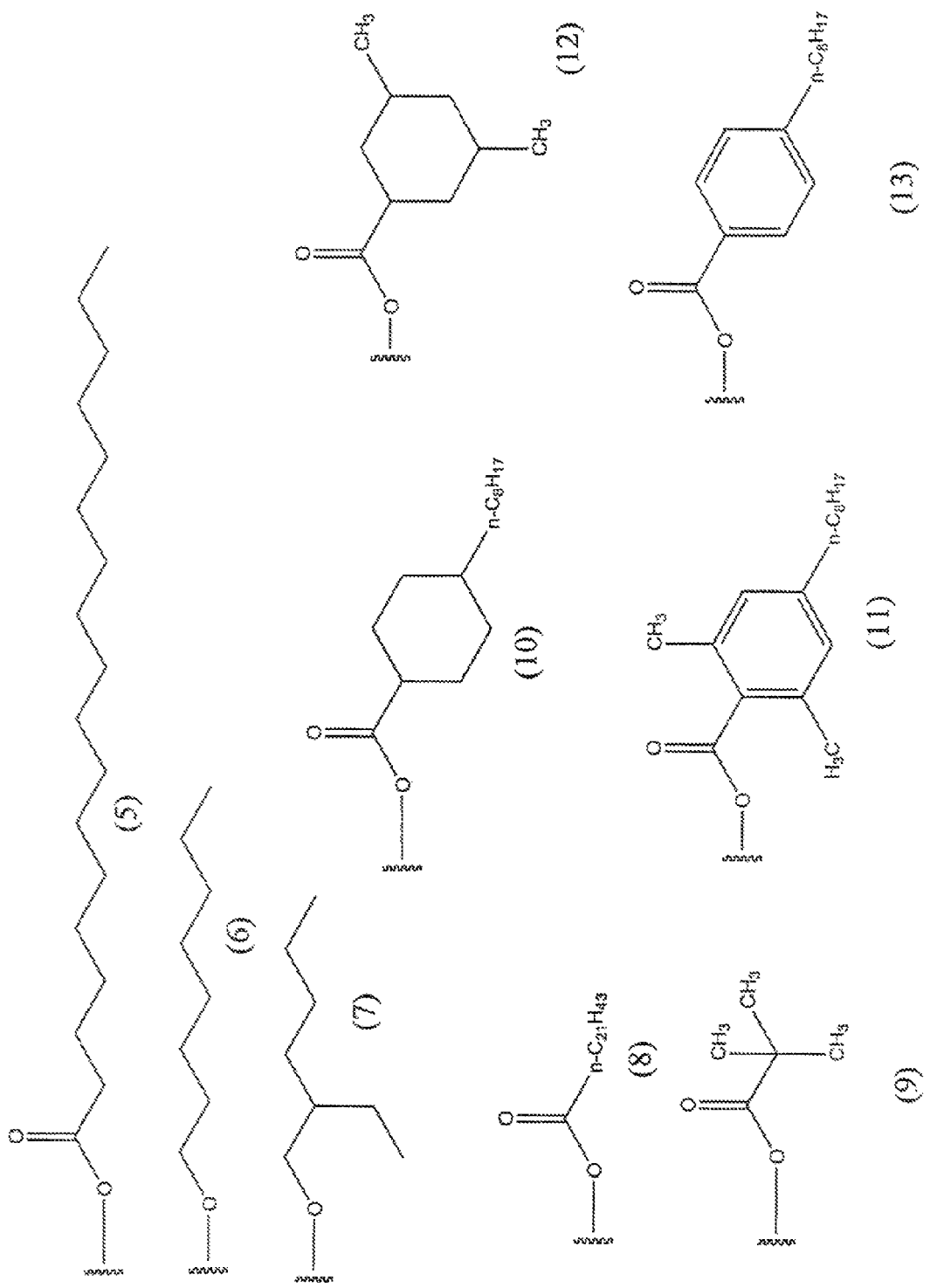
FIGS. 7-9 shows various substitution groups for violanthrones and isoviolanthrones.

Referring to FIG. 7, in some embodiments, one or more substitution groups of a violanthrone or an isoviolanthrone is or has an ester or an ether group, as shown in groups (5)-(13). Of those, generally the ethers and esters that include alkyl and cylcoalkyl portions are favored because they can impart enhanced solubility to the tagging compounds. Compounds (5) and (6) are commercially available from Aldrich Chemical Company.

Figure 8:
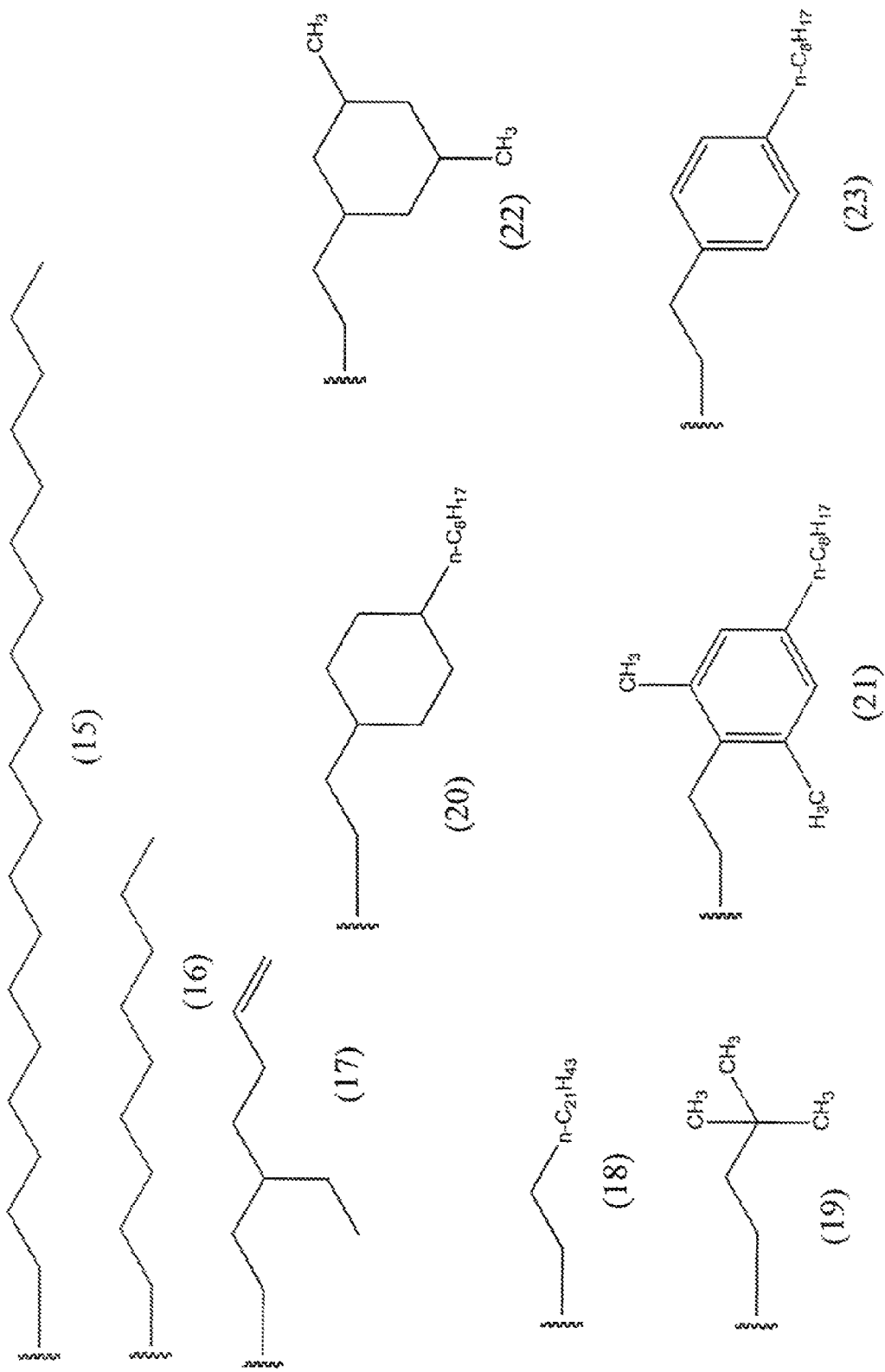

Referring now to FIG. 8, in other embodiments, one or more substitution groups of a violanthrone or an isoviolanthrone is a hydrocarbon fragment, as shown in substitution groups (15)-(23). For example, the hydrocarbon fragment can be straight chain, branched, mono- or poly-cyclic alkyl. Examples of straight chain and branched alkyl include methyl, ethyl, propyl, isopropyl, butyl, isobutyl, sec-butyl, t-butyl, amyl, isoamy, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5- ethylheptyl 1-, 2- or 3-propylhexyl, decyl, 1-, 2-, 3-, 4-, 5-, 6-, 7- nand 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3- 4-, 5-, 6- or 7-ethylnonyl, 1- , 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8ethyldecyl, 1-, 2-, 3-, 4-, 5- or 6-propylnonyl, 1-, 2-, 3- or 4-butyloctyl, and 1,2-pentylheptyl. Examples of cyclic alkyl groups include cyclopropyl, cyclobutyl, cyclopentyl, cyclohexyl, cycloheptyl, cyclooctyl, cyclononyl, and cyclondecyl. For example, the hydrocarbon fragment can straight chain, branched, mono- or poly-cyclic alkenyl. Examples of alkenyl groups include vinyl, allyl, 1-methylvinyl, butenyl, iso-butenyl, 3-methyl-2-butenyl, 1-pentenyl, cyclopentenyl, 1-methylcyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentagienyl, 1,3-hexadienyl, 1,4-hexadienyl, 1,3-cyclohexadienyl, 1,4-cyclohexadienyl, 1,3-cyclohoptadienyl, 1,3, 5-cycloheptatrienyl, and 1,3,5,7-cyclooctatetraenyl. For example, the hydrocarbon fragment can be aryl. Examples of aryl include phenyl, biphenyl, naphthyl, anthracenyl, benzanthracenyl, dibenzanthracenyl, and phenantrenyl.

Figure 9:
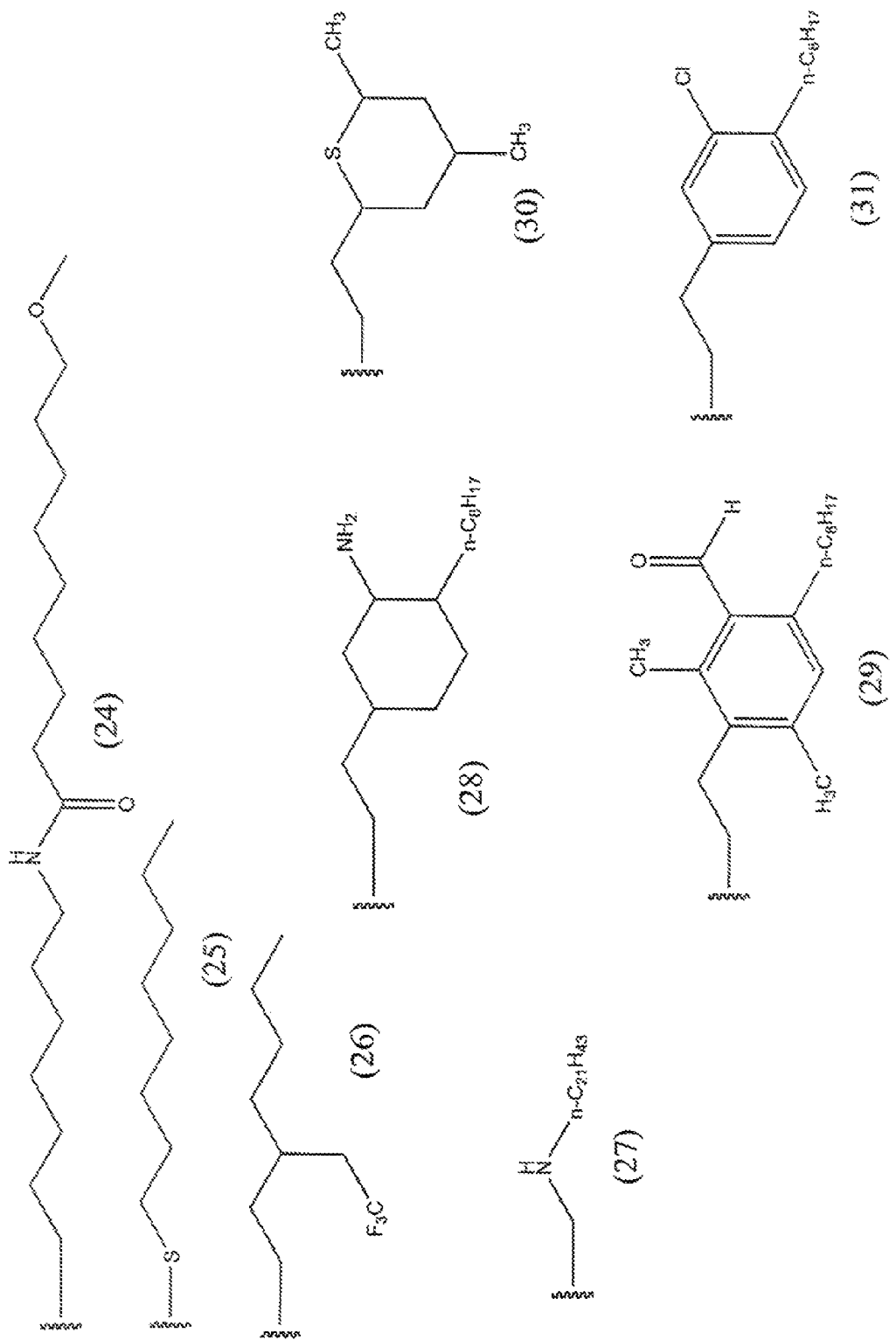

Referring now to FIG. 9, in some embodiments, one or more substitution groups of a violanthrone or an isoviolanthrone can have heteroatom substitution, such as O, N, S, F, or Cl. For example, the O can be configured in an ether or an ester group, the nitrogen can be configured in an amino or amide group and the S can be configured in a thiol or thioether group. Specific examples include substitution groups (24)-(31).

Figure 10:
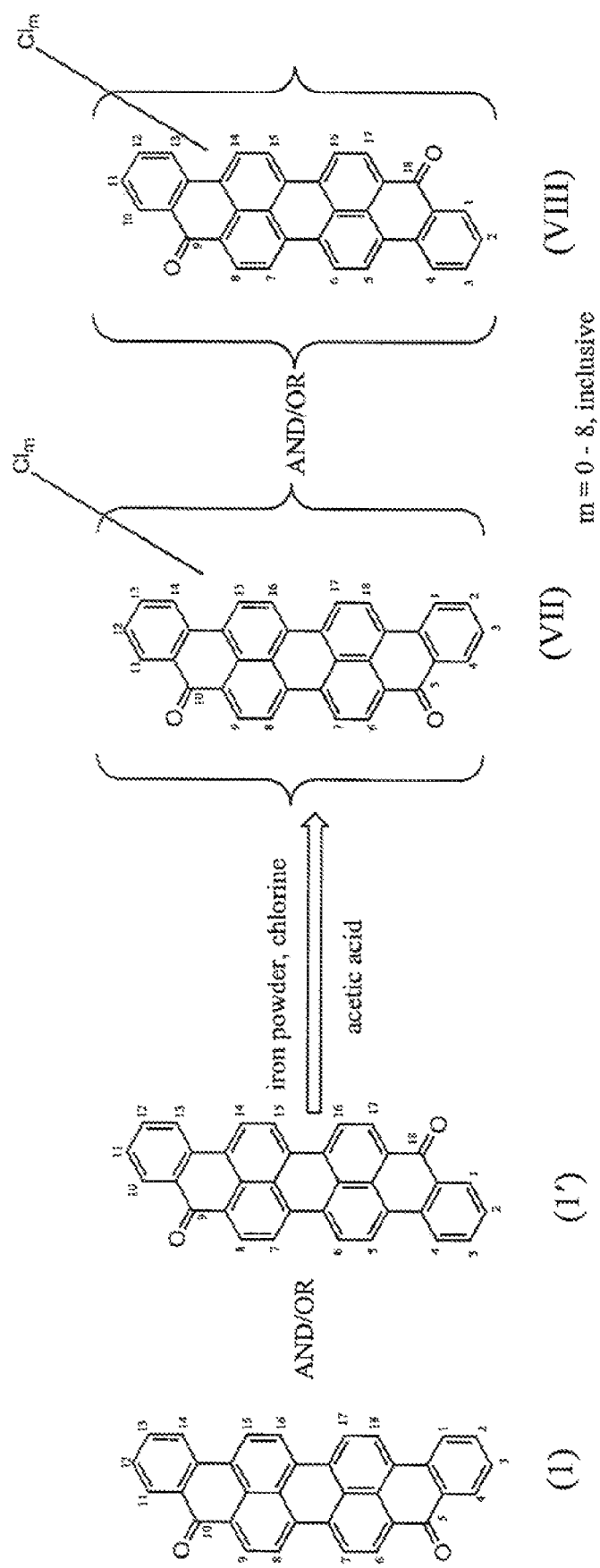
FIG. 10 shows a synthetic method for making chlorinated violanthrones (VII) and/or isoviolanthrones (VIII).

Referring now to FIG. 10, chlorinated derivatives of violanthrone (VII) and/or isoviolanthrone (VIII) can be made by treating violanthrone (1) and/or isoviolanthrone (1') with chlorine in the presence of a metal, such as iron powder. Generally, the reaction is carried out in an organic acid solvent, such as acetic acid. In such a procedure, by altering reaction conditions, low levels of chlorination can be obtained, e.g., m being 1, 2, or 3 in Structure (VII) and/or (VIII), or high levels chlorination can be obtained, e.g., m being 4, 5, 6, 7 or even 8. Generally, higher levels of chlorine and/or higher reaction temperatures favor more highly chlorinated products. Chlorination schemes are discussed in U.S. Pat. No. 5,554,774, issued Sep. 10, 1996, to Bergmann et al.

Figure 11:
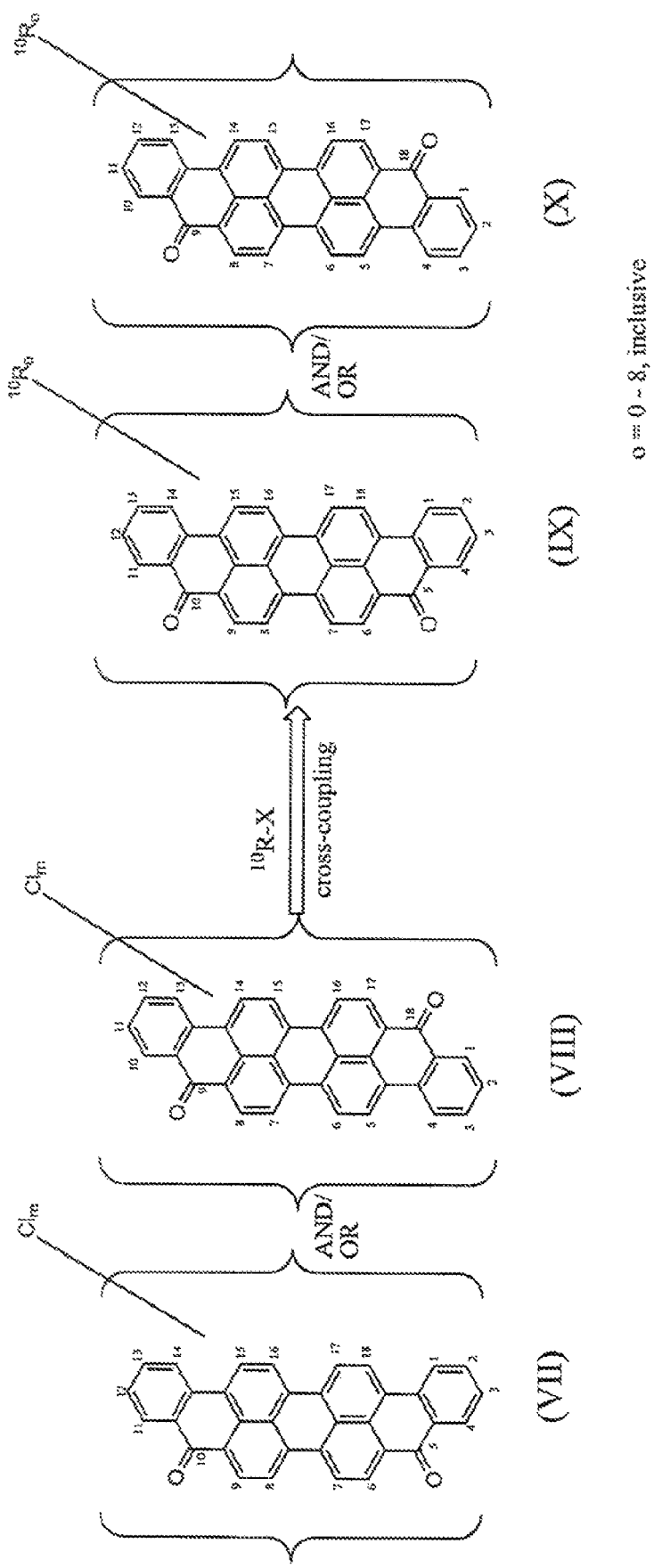
FIG. 11 shows a synthetic method for making substituted violanthrones (IX) and/or isoviolanthrones (X) via cross-coupling.

Referring now to FIG. 11, hydrocarbon derivatives, e.g., alkylated derivatives, of violanthrone (IX) and/or isoviolanthrone (X) can be made by treating the chlorinated derivatives of violanthrone (VII) and/or isoviolanthrone (VIII) with a halide ($^{10}$R-X), e.g., an alkyl halide, in the presence of a cross-coupling catalyst such as copper powder. In such resulting compounds, $^{10}R_0$ can be any of the hydrocarbon fragments described herein.

Figure 12:
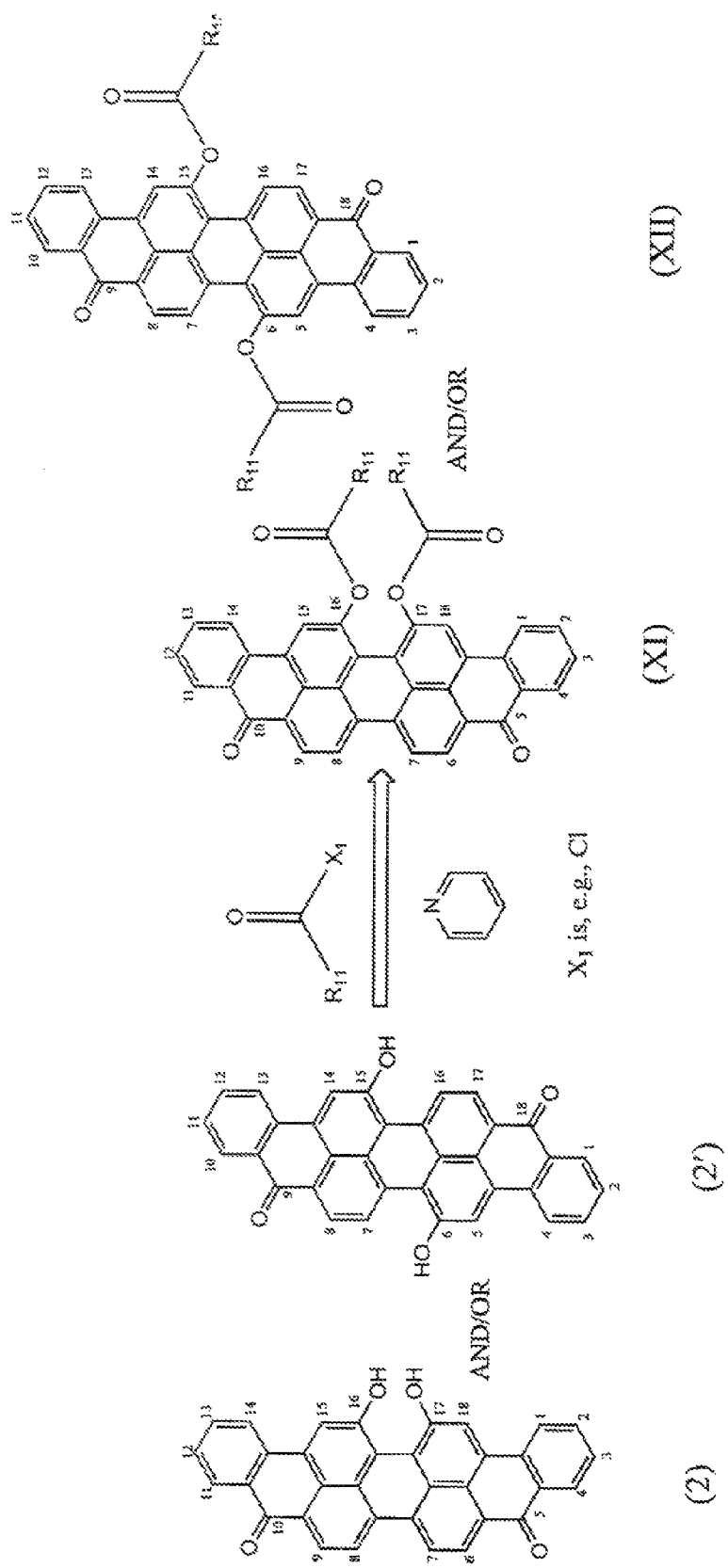
FIG. 12 shows a synthetic method for making 16,17-diester-functionalized violanthrones (XI) and/or 6,15-diester-functionalized isoviolanthrones (XII).

Referring now to FIG. 12, ester derivatives of violanthrone (XI) and/or isoviolanthrone (XII) can be made by treating 16,17-dihydroxyviolanthrone and/or 6,15-dihydroxyisoviolanthrone, respectively, with an acid halide ($R_{11}$(CO)X) in the presence of a strong, non-nucleophilic base, such as pyridine, $R_{11}$ can be any of the hydrocarbon fragments discussed herein. Esterification of hydroxyviolanthrones and hydroxyisoviolanthrones is described in more detail in U.S. Pat. No. 4,486,587, issued Dec. 4, 1984 to Seybold.

Figure 13:
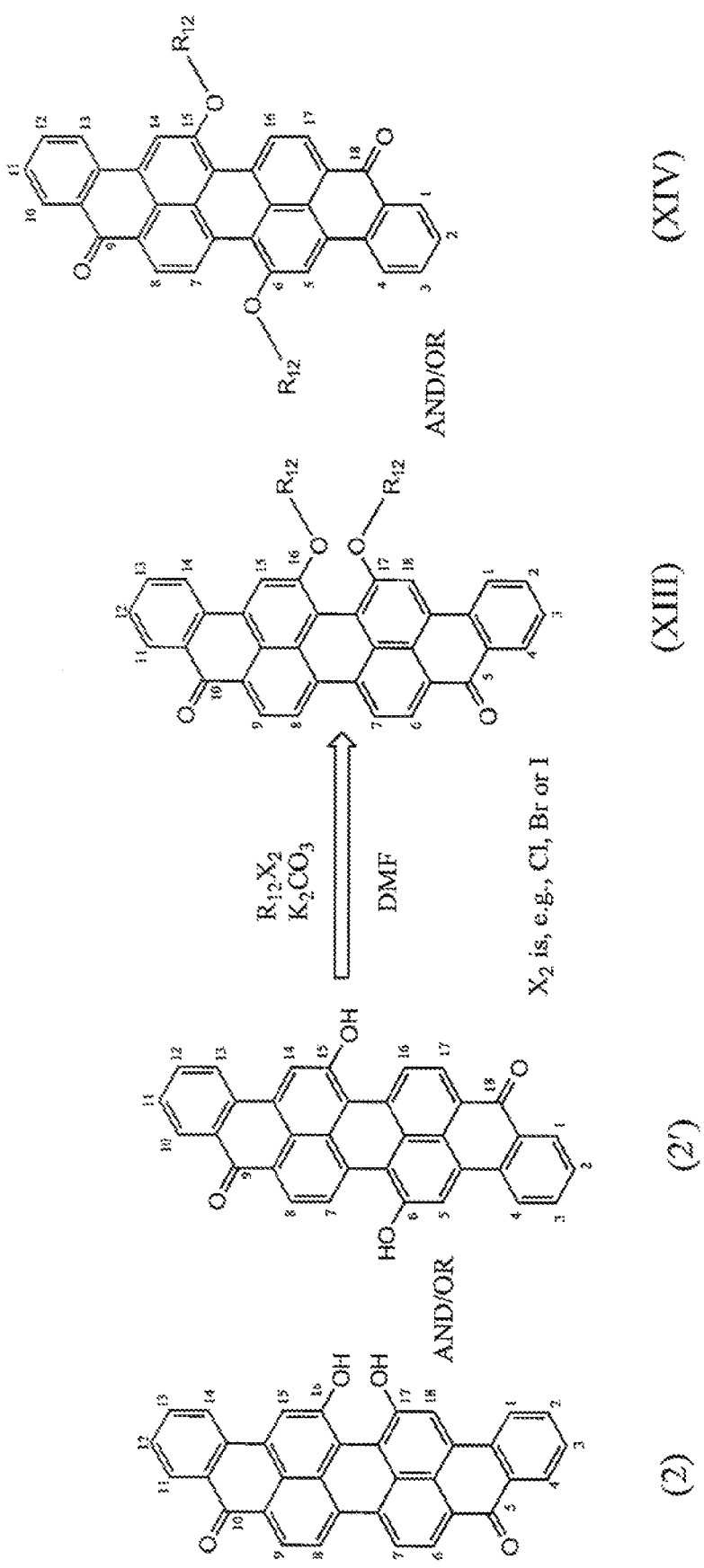
FIG. 13 shows a synthetic method for making 16.17-diether-functionalized violanthrones (XIII) and/or 6,15-diether-functionalized isoviolanthrones (XIV).

Referring now to FIG. 13, ether derivatives of violanthrone (XIII) and/or isoviolanthrone (XIV) can be made by treating 16,17-dihydroxyviolanthrone and/or 6,15-dihydroxyisoviolanthrone, respectively, with an halide ($R_{12}X_2$), e.g., an alkyl halide, in the presence of a carbonate, such as $K_2CO_3$. Generally, the reaction is carried out in a polar solvent such as dimethyl formamide (DMF) or dimethyl sulfoxide (DMSO). $R_{12}$ can be any of the hydrocarbon groups discussed herein. Etherification of hydroxyviolanthrones and hydroxyisoviolanthrones is described in more detail in U.S. Pat. No. 4,486, 587, issued Dec. 4, 1984, to Seybold.

Figure 14:
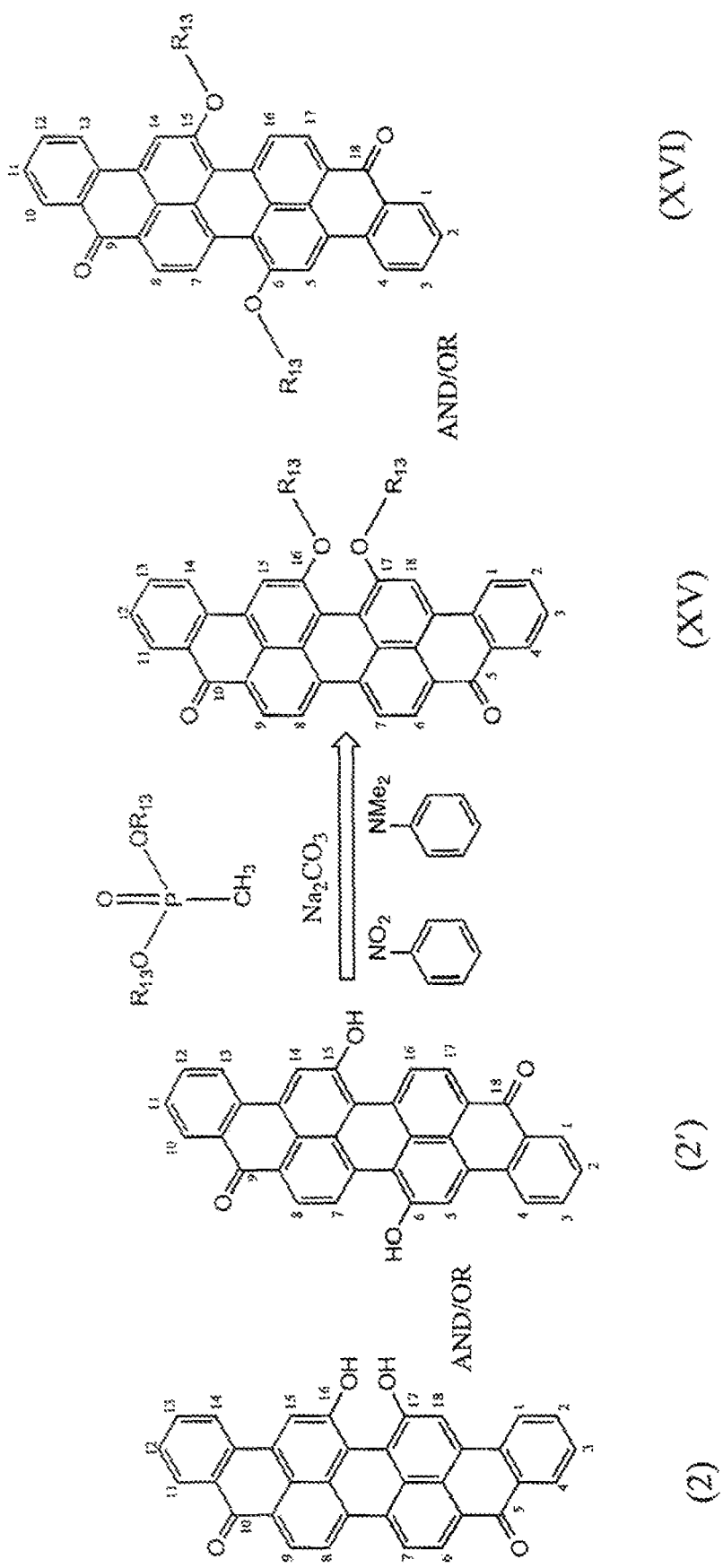
FIG. 14 shows a alternative synthetic method of making 16,17-diether-functionalized violanthrones (XV) and/or 6,15-diether-functionalized isoviolanthrones (XVI).

Referring now to FIG. 14, in an alternative procedure, ester derivatives of violanthrone (XV) and/or isoviolanthrone (XVI) can be made by treating 16,17-dihydroxyviolanthrone and/or 6,15-dihydroxyisoviolanthrone, respectively, with an dialkyl alkanephosphonate, such as a dialky methylphosphonate (($R_{13}$O)$_2$P(O)CH$_3$), in the presence of a carbonate, such as $K_2CO_3$. Generally, the reaction is carried out in a polar solvent, such as nitrobenzene, in the presence of a non-nucleophilic base, such as N,N-dimethylaniline. $R_{13}$ can be any of the hydrocarbon groups described herein. This alternative etherification is described in more detail in U.S. Pat. No. 4,198,529, issued Apr. 15, 1980, to Grelat et al.

Generally any of the tagging compounds described herein absorb and/or emit in the near infrared region of the spectrum, e.g., between about 600 nm and about 1000 nm, between about 650 nm and 950 nm or between about 700 nm and 900 nm.

As an overview, to detect a tagging compound in a tagged product, a tagged petroleum product having any one or more of the violanthrones and/or isoviolanthrones described herein is selected, and then the tagging compound is detected. For detection, generally the concentration of the tagging compound in the petroleum product should be at least about 1 ppb by weight.

The tagging compound can be detected by a response of the tagging compound. For example, the response can be emissions from the tagging compound, absorbances by the tagging compound, or even emissions from a reaction product formed by reacting the tagging compound with another compound.

Figure 15:
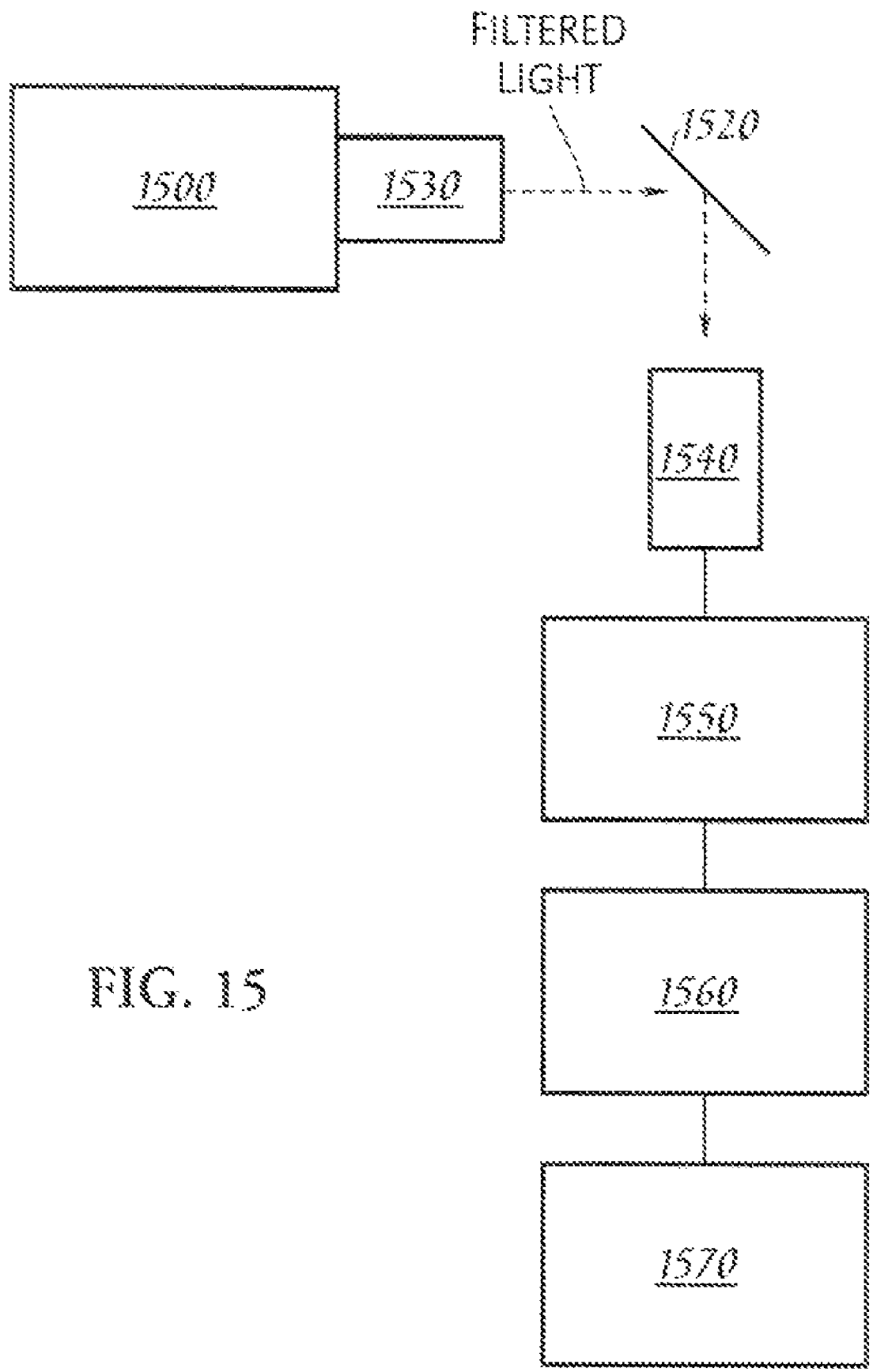
FIG. 15 is a schematic representation of a fluorometer.

For example, FIG. 15 shows an apparatus useful for detecting, identification, and/or quantifying the tagging compounds in a tagged petroleum product. The apparatus includes a light source 1500 that emits radiation in the visible and near infrared region. The light source 1500 can be a multi-wavelength light source or it may be a tuned laser having a narrow band of wavelengths. After passing through a wavelength selector 1530 (e.g., monochromator or interference filter), the light from light source 1500 can illuminate the tagging compound or compounds in the tagged petroleum product placed on a stage 1520. A second wavelength selector 1540 and photo detector 1550 can be placed at a 90 degree angle (relative to the direction of light shinning on stage 1520). Having the light source 1500, wavelength selectors 1530 and 1540, and photodector 1550 arranged on two sides of a triangle (as shown), minimizes scattered light entering the detector. After passing through the photodetector 1550, the light passes through an amplifier 1560, and then onto a digital multimeter 1570 for detection. The output of the digital multimeter is connected to a computer and a display (not shown) to provide for numerical and graphical indication of the amount of luminous flux at the predetermined wavelength emitted and/or absorbed by the tagging compound or compounds in the petroleum products.

Figure 16:
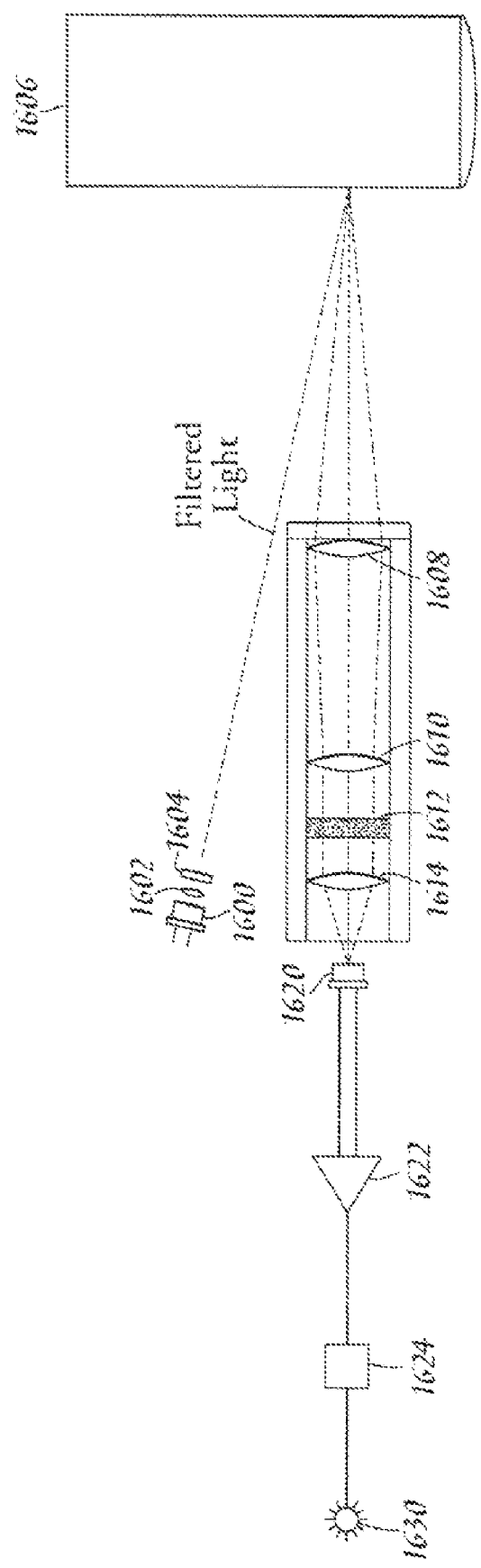
FIG. 16 is a schematic representation of fluorometer utilizing a laser diode light source and an LED indicator.

FIG. 16 shows another apparatus useful for detecting, identification, and/or quantifying the tagging compounds in a tagged petroleum product. The apparatus has a laser diode light source 1600 that can emit radiation in the near infrared region. The light from the laser diode light source 1600 can be collimated through a collimating lens 1602, can pass through a filter 1604, and can then illuminate the tagged petroleum product 1606. Thereafter, the light can pass through a focusing lens 1608, followed by a first compressing lens 1610, a filter 1612, and then a second compressing lens 1614. The angle between the light striking the petroleum product 1606 and the focusing lens, compressing lenses and filter can define an angle of about 30 degrees or less, which tends to minimize scattered light. After passing through the second compressing lens, the light can strike a photodetector 1620. The signal from the photodetector 1620 can be amplified with a current-to-voltage converter 1622. The output from the amplifier 1622 can then be detected by a threshold detector 1624, which can be configured to minimize any interference from untagged materials. Furthermore, the presence of tagged compound or compounds can be indicated by a light-emitting diode (LED) indicator 1630.

In some embodiments, the emission and/or the absorbance is quantified to determine the concentration of the tagging compound or compounds. For example, the absorbance can be quantified by integration of the detected signal, and then comparing the integrated signal to a calibration curve. In some embodiments, a full spectrum is obtained of the tagging compound or compounds to obtain a fingerprint of the tagging compound or compounds. In some embodiments, at least two tagging compounds are utilized and a ratio of their emission and/or absorbance is used to determine authenticity of a sample.

In some embodiments, emission and/or absorbance data is collected on the tagging compound or compounds, and then the data collected is compared to data for a library of tagging compounds to identify a source of the tagged product.

In some embodiments, the response includes a chemiluminescent emission from a reaction product generated by a reaction of the tagging compound with another compound, such as an oxidizing agent, e.g., a peroxide and/or an oxalate. For example, in one embodiment, chemiluminescence is generated by mixing the tagged petroleum product with an oxalate, e.g., bis(6-carbopentoxy-2,4,5-trichlorophenyl) oxalate, and a peroxide material, e.g., hydrogen peroxide in combination with sodium salicylate. Chemiluminescent systems are described by Vega, U.S. Pat. No. 4,076,645, issued Feb. 28, 1978, to Vega: U.S. Pat. No. 4,313,843, issued Feb. 2, 1982, to Bollyky et al., and, U.S. Pat. No. 4,678,608, issued Jul. 7, 1987, to Dugliss.

EXAMPLES

The disclosure is further described in the following example, which does not limit its scope.

Figure 17:
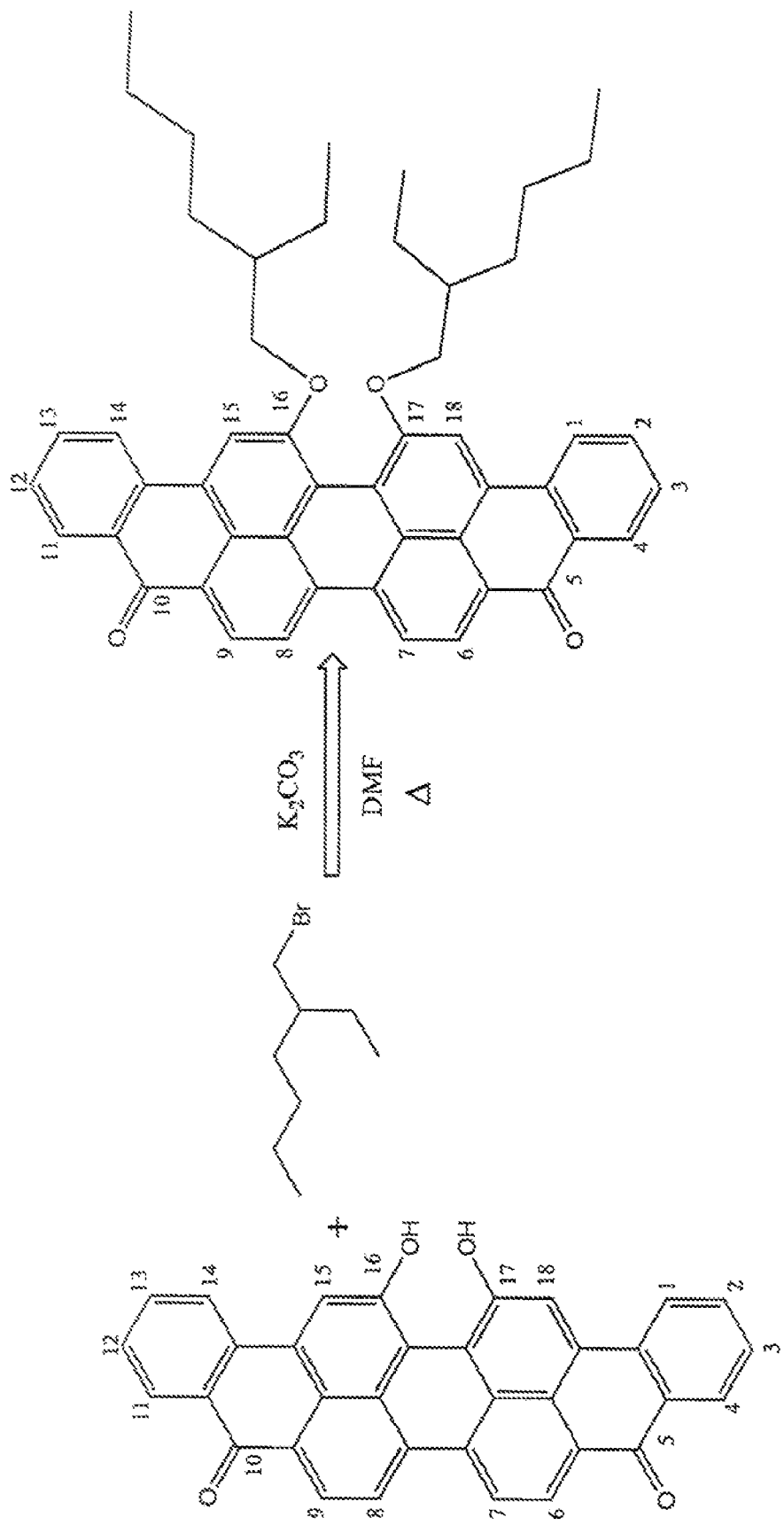
FIG. 17 shows a synthetic method of producing a 16,17 di-2-ethylhexyl ether (7) from 16,17-dihydroxyviolanthrone (2) and 2-ethylhexyl bromide.

Preparation of the 16,17-di-2-ethylhexyl ether (7) of 16,17-di-hydroxy violanthrone (2). Referring to FIG. 17, to a flask containing 50 mL of dry dimethyl formamide (DMF) was added 2.14 mmol (1.04 g) of 16,17-dihydroxyviolanthrone (2) (FW=488.49 g/mol), which was obtained from Pfaltz and Bauer Chemical Company and used as received. To this was added 6.52 mmol (1.26 g) of dry 2-ethylhexyl bromide (FW=193.13 g/mol), which was obtained from Aldrich Chemical and used as received. To this mixture was added 6.80 mmol (0.940 g) of potassium carbonate (FW=138.21 g/mol). The entire contents of the flask were heated for 20 hours at 100° C. This layer chromatography (TLC) on alumina (solvent=5 percent acetone in toluene) after the 20 hours revealed two spots, one small green spot consistent with starting compound (2) and a larger, farther traveled blue spot consistent with the desired ether (7).

After the 20 hour reaction period, 300 mL of water was added to the contents of the flask, which was acidified using several drops of concentrated sulfuric acid. After acidification, the solution was clear with a fine, dark participate suspended therein. The dark precipitate was captured on a glass frit, to produce a dark, solid cake of material.

To remove traces of the starting diol (2), the solid cake was treated with chloroform to re-solubilize the desired product (7) (diol (2) being insoluble in chloroform), and then the chloroform extract was dried over magnesium sulfate. The magnesium sulfate was filtered away and the solvent was removed with a rotary evaporator. A small amount of liquid remained after removal of the chloroform (likely DMF and/or 2-ethylhexyl bromide), which was removed under high vacuum, giving 1.28 mmol (0.910 g, 60 percent yield) of a dark blue, crystalline solid of the desired compound (7) (FW=712.91 g/mol).

The purified compound (7) above can be added to a petroleum prouct for tagging, or a concentrate of the purified product can be produced, which can latter be added to a petroleum product for tagging.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A tagged product comprising:
   (a) a petroleum product; and
   (b) a tagging compound selected from a group consisting of Structure I and Structure II, wherein Structure I is

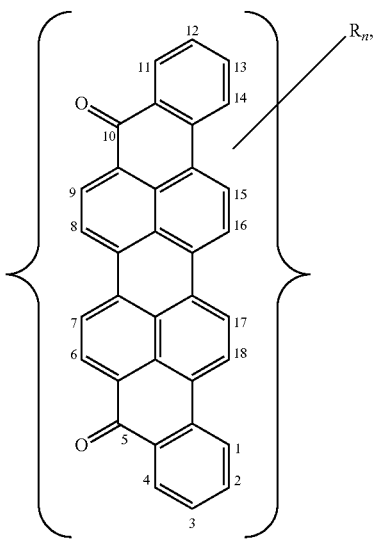

wherein Structure II is

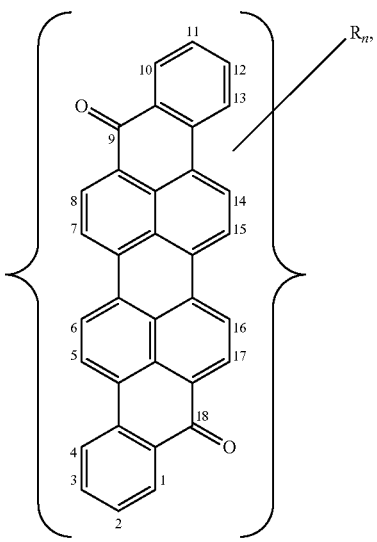

and wherein
   (i) a concentration of between about 1 ppb and about 1000 ppb by weight of said tagging compound is dissolved in the petroleum product,
   (ii) each R of $R_n$ is independently selected from a group consisting of OH, SH, $NH_2$, $NO_2$, F, Cl, Br, I, and moieties comprising between 1 and 36 carbon atoms, inclusive, wherein at least one R is a first moiety that comprises between 1 and 36 carbon atoms, inclusive, and said first moiety is an ether group;
   (iii) n is an integer between 1 and 8, inclusive; and
   (iv) the tagging compound responds to near infrared light, wherein said response is (A) the tagging compound absorbs the near infrared light between about 600 nm and about 1000 nm, (B) the tagging compound emits near infrared light between about 600 nm and about 1000 nm, or (C) a combination thereof.

2. The tagged product of claim 1, wherein the tagging compound in the tagged product is invisible to the naked eye such that the color of the petroleum product and the color of the tagged product are not appreciably different.

3. The tagged product of claim 1, wherein the first moiety defines a ring.

4. The tagged product of claim 1, wherein the petroleum product is selected from the group consisting of gasoline, kerosene, diesel, naphtha, lubricant oil and furnace oil.

5. The tagged product of claim 1, wherein the response of the tagging compound to near infrared light is (A) the tagging compound absorbs the near infrared light between about 650 nm and about 950 nm, (B) the tagging compound emits near infrared light between about 650 nm and about 950 nm, or (C) a combination thereof.

6. The tagged product of claim 1, wherein the response of the tagging compound responds to near infrared light is (A) the tagging compound absorbs the near infrared light between about 700 nm and about 900 nm, (B) the tagging compound emits near infrared light between about 700 nm and about 900 nm, or (C) a combination thereof.

7. The tagged product of claim 1, wherein the first moiety is a di-2-ethylhexyl ether group.

8. The tagged product of claim 1, wherein the first moiety comprises only atoms selected from the group consisting of carbon, hydrogen and oxygen.

9. A tagged product comprising:
   (a) a petroleum product; and
   (b) a tagging compound selected from a group consisting of Structure I and Structure II, wherein Structure I is

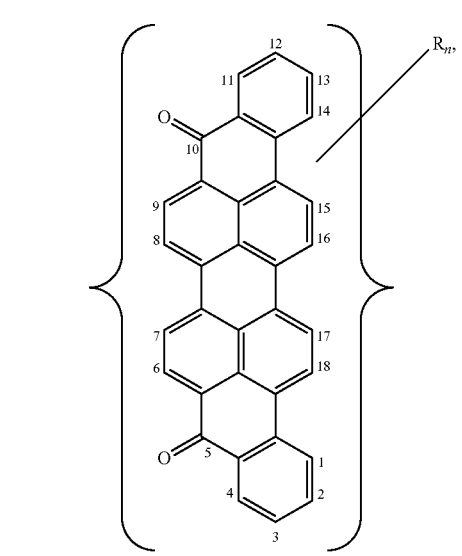

wherein Structure ll is

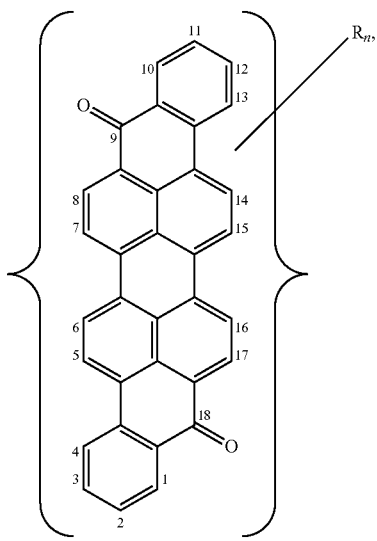

and wherein
(i) a concentration of between about 1 ppb and about 1000 ppm by weight of said tagging compound is dissolved in the petroleum product,
(ii) each R of $R_n$ is independently selected from a group consisting of OH, SH, $NH_2$, $NO_2$, F, Cl, Br, I, and moieties comprising between 1 and 36 carbon atoms, inclusive, wherein at least one R is a first moiety that comprises between 1 and 36 carbon atoms, inclusive, and said first moiety comprises only atoms selected from the group consisting of carbon and hydrogen,
(iii) n is an integer between 1 and 8, inclusive, and
(iv) the tagging compound responds to near infrared light, wherein said response is (A) the tagging compound absorbs the near infrared light between about 600 nm and about 1000 nm, (B) the tagging compound emits near infrared light between about 600 nm and about 1000 nm, or (C) a combination thereof.

10. The tagged product of claim 9, wherein said first moiety is selected from the group consisting of C1-C21 alkyl, C1-C8 cylcoalkyl, C1-C21 alkenyl, C1-C10 aryl and C1-C21 alkylaryl.

* * * * *

UNITED STATES PATENT AND TRADEMARK OFFICE
CERTIFICATE OF CORRECTION

| | | |
|---|---|---|
| PATENT NO. | : 8,129,190 B2 | Page 1 of 1 |
| APPLICATION NO. | : 11/561119 | |
| DATED | : March 6, 2012 | |
| INVENTOR(S) | : Philip Forshee and Peter Kottenstette | |

It is certified that error appears in the above-identified patent and that said Letters Patent is hereby corrected as shown below:

Title Page:

Item [73], delete "Applied Nanotech Holdings, Inc., Austin, TX (US)" and substitute the following:

Authentix, Inc., Addison, TX (US)

Signed and Sealed this

Thirty-first Day of July, 2012

David J. Kappos
*Director of the United States Patent and Trademark Office*